United States Patent
Andersen (10) Patent No.: US 8,414,868 B2
(45) Date of Patent: Apr. 9, 2013

(54) IN SITU FOAMABLE DENTAL BLEACHING COMPOSITIONS AND METHODS, SYSTEMS AND KITS FOR BLEACHING TEETH USING SUCH COMPOSITIONS

(75) Inventor: Scot N. Andersen, Draper, UT (US)

(73) Assignee: Ultradent Products, Inc., South Jordan, UT (US)

( * ) Notice: Subject to any disclaimer, the term of this patent is extended or adjusted under 35 U.S.C. 154(b) by 102 days.

(21) Appl. No.: 12/700,197

(22) Filed: Feb. 4, 2010

(65) Prior Publication Data

US 2011/0189637 A1 Aug. 4, 2011

(51) Int. Cl.
- *A61K 8/33* (2006.01)
- *A61K 8/81* (2006.01)
- *A61K 8/22* (2006.01)
- *A61C 17/00* (2006.01)

(52) U.S. Cl. .............. 424/53; 424/49; 433/216

(58) Field of Classification Search .......... 424/45, 424/49, 73, 450; 141/20
See application file for complete search history.

(56) References Cited

U.S. PATENT DOCUMENTS

| | | | |
|---|---|---|---|
| 3,976,223 A * | 8/1976 | Jass et al. ................ | 222/94 |
| 5,665,332 A | 9/1997 | Mundschenk et al. | |
| 6,139,820 A | 10/2000 | Fischer et al. | |
| 6,331,291 B1 | 12/2001 | Glace et al. | |
| 6,905,673 B2 | 6/2005 | Rajaiah et al. | |
| 7,060,253 B1 | 6/2006 | Mundschenk | |
| 2003/0232023 A1 | 12/2003 | Arnold | |
| 2004/0197270 A1 | 10/2004 | Mundschenk | |
| 2004/0247534 A1 | 12/2004 | Stoltz | |
| 2005/0005995 A1 * | 1/2005 | Pericard .................. | 141/20 |
| 2005/0214720 A1 | 9/2005 | Milanovich et al. | |
| 2006/0093558 A1 * | 5/2006 | Lin et al. ................... | 424/47 |
| 2006/0147406 A1 * | 7/2006 | Yerby et al. ............ | 424/70.24 |
| 2008/0025926 A1 | 1/2008 | Kavouklis et al. | |
| 2008/0050408 A1 | 2/2008 | Hayman et al. | |
| 2008/0063612 A1 | 3/2008 | MacDonald et al. | |

FOREIGN PATENT DOCUMENTS

| | | | |
|---|---|---|---|
| JP | 09295923 | | 11/1997 |
| JP | 2001172144 | | 6/2001 |
| WO | WO01/62210 | * | 8/2001 |

OTHER PUBLICATIONS

Instruments/Preventives, based on information and belief, available at least as early as Jun. 2008 at the following website: www.jrdentalsupplies.com.

New Aquafresh Iso-Active Foaming Gel works beyond paste, based on information and belief, available at least as early as Jun. 2008 at the following website: www.aquafresh.com.uk/isoactive.

Lindal Group: All about Aerosols, based on information and belief, available at least as early as Jan. 2010 at the following website: http://www.lindalgroup.com/en.product_354.php.

* cited by examiner

*Primary Examiner* — Walter Webb
(74) *Attorney, Agent, or Firm* — Workman Nydegger

(57) ABSTRACT

In situ foamable dental bleaching compositions include a dental bleaching agent, thickening agent, polyol, and in situ foaming agent. The foamable dental bleaching compositions are initially dispensed as a dental bleaching gel. Upon placement of the dental bleaching gel onto a person's tooth surfaces, the in situ foaming agent causes the bleaching gel to foam. Dental bleaching systems include an in situ foamable dental bleaching composition within a pressurized container (e.g., bag-on valve container) having a nozzle that, when actuated, expels the in situ dental bleaching composition as a gel. Dental bleaching methods include dispensing the in situ foamable dental bleaching composition as a gel, contacting a person's tooth surfaces with the dental bleaching gel, and allowing the gel to expand and foam in order to dynamically distribute and replenish the dental bleaching agent to the tooth surfaces and into the interproximal spaces between teeth.

26 Claims, 3 Drawing Sheets

IN SITU FOAMABLE DENTAL BLEACHING COMPOSITIONS AND METHODS, SYSTEMS AND KITS FOR BLEACHING TEETH USING SUCH COMPOSITIONS

BACKGROUND OF THE INVENTION

1. The Field of the Invention

The present invention is in the field of dental bleaching compositions, systems and methods for whitening a person's teeth. The invention relates to dental bleaching compositions that are dispensed and applied to tooth surfaces as a gel and then foam in situ on the tooth surfaces.

2. The Relevant Technology

To achieve whiter teeth, people often have their teeth covered with veneers or chemically bleached. A conventional dental professional bleaching process generally involves: (1) making an alginate impression of the patient's teeth; (2) making a stone cast or model of the impression; (3) vacuum forming a dental tray from the model, usually from a heated sheet of thin ethyl vinyl acetate (EVA) material; (4) trimming the upper tray rim to exclude gingival coverage; (5) introducing a bleaching gel into the tray; and (6) placing the tray over the teeth to be bleached for a suitable time period to effect tooth bleaching.

Because of the time and cost associated with forming customized trays, less time consuming and costly alternatives have been developed. Examples include boil and bite trays and non-custom trays, both of which tend to bulky and uncomfortable, flexible strips, which have a tendency to slip off the teeth, and paint-on bleaching compositions, which are directly exposed to saliva in a person's mouth.

Dental bleaching compositions are usually in the form of a liquid or gel. Liquid bleaching compositions do not provide adhesion to teeth and can run out of the tray used to apply the composition. Gel bleaching composition, particularly those which are sticky and viscous, are better able adhere to a person's teeth and can assist in holding a dental tray over the teeth during treatment. Maintaining good adhesion to a person's teeth is believed to provide superior bleaching by maintaining continuous contact between the bleaching composition and the person's teeth. In reality, the inventors discovered that dental bleaching gels, particularly those which are stiff and highly viscous, can become depleted of bleach at the contact interface with the tooth surfaces, requiring removal and reapplication of bleaching gel to complete the bleaching process. Finally, there are foamable bleaching compositions such as toothpastes that include a surfactant foaming agent that generates foam while brushing by mixing the toothpaste with saliva in the person's mouth.

BRIEF SUMMARY OF THE INVENTION

The present invention is directed to dental bleaching compositions that are formulated so as to be dispensed and applied to a person's tooth surfaces in the form of a gel and that expands and forms a foamed bleaching composition in situ on the tooth surfaces. The invention also includes delivery systems, kits and methods that utilize the inventive dental bleaching compositions described herein.

Applying the dental bleaching composition as a gel provides essentially full contact and good adhesion between the composition and the tooth surfaces to be bleached, thereby maximizing the amount of dental bleaching agent that initially comes into contact with and adheres to the person's teeth. The gel bleaching composition then forms a foamed gel composition in situ as a result of ambient heat contained in or on the patient's mouth and teeth. The foaming action further activates the dental bleaching composition and better distributes the bleaching agent over the teeth and into the interproximal spaces between the teeth. It is believed that the foaming action creates internal stirring of the bleaching composition via disruption of the gel matrix, thereby enhancing the availability of the active dental bleaching agent for bleaching teeth.

The in situ foaming of the bleaching composition makes the bleaching agent more readily available for tooth bleaching compared to gel bleaching compositions that do not foam in situ after being placed onto the tooth surfaces. And it does so passively without having to brush or mechanically agitate the composition. This permits the composition to be applied using dental trays and strips. Also, by initially coating the tooth surfaces with a bleaching composition that is in the form of a gel prior to foaming, the in situ foamable bleaching compositions provide superior contact between the dental bleaching agent and tooth surfaces, and therefore providing superior bleaching, compared to bleaching compositions that are dispensed as an aerosol foam and applied to teeth in an already foamed condition. The foaming action while on the teeth provides chemical stirring, which replenishes the contact surface area between the bleaching composition and teeth with fresh bleaching agent. This increases the availability of bleaching agent for bleaching teeth compared to non-foamable compositions.

Dental bleaching compositions according to the invention typically include a dental bleaching agent, a thickening agent, a polyol, an in situ foaming agent, and other adjuvents as desired. Examples of useful bleaching agents include aqueous hydrogen peroxide, peroxide generating compounds such as carbamide peroxide, calcium peroxide, sodium perborate, and sodium percarbonate, and other compounds that can release active oxygen radicals to effect tooth bleaching. One example of a non-peroxide bleaching agent is sodium chlorite, which forms chorine dioxide when mixed with water, which in turn decomposes and releases active oxygen radicals useful in bleaching teeth.

Examples of useful thickening agents include polyvinyl pyrrolidone (PVP), carboxypolymethylene, polyethylene oxide, polyacrylic acid polymers or copolymers, polyacrylates, polyacrylamides, copolymers of polyacrylic acid and polyacrylamide, PVP-vinyl acetate copolymers, carboxymethylcellulose, carboxypropylcellulose, polysaccharide gums, fumed silica, fumed alumina, and the like.

Examples of useful polyols include glycerin, propylene glycol, polyethylene glycol, 1,3-propane diol, polypropylene glycol, xylotol, and the like.

An example of a useful in situ foaming agent is isopentane. Isopentane is advantageous as it has a boiling point (i.e., 28° C.) that is slightly higher than room temperature (i.e., 20° C.) but less than body temperature (i.e., 37° C.). That permits the inventive dental bleaching compositions to be dispensed as a gel and then foam in situ when contacted with a person's teeth. Other in situ foaming agents that can be used include other hydrocarbons having similar boiling points, such as pentane.

The compositions may be aqueous or non-aqueous. If non-aqueous, the composition will typically include a relatively large quantity (e.g., at least about 50%) of a polyol.

The amounts of the foregoing components are advantageously adjusted in order to yield a dental bleaching composition that is not initially dispensed as a foamed composition from a pressurized contain or other vessel, but rather foams in situ after being placed into contact with a person's teeth. Alternatively, the foamable dental bleaching composition may expand slightly upon being discharged from a pressurized container and then further expand and foam after being applied to a person's teeth.

Ideally, the composition can exist as a gel at room temperature and only foams when heated to a temperature above room temperature (e.g., to a temperature of at least about 26° C., preferably at least about 28° C., more preferably at least about 30° C.). The identities and/or amounts of the thickening agent, bleaching agent, polyol, and in situ foaming agent are selected to achieve this result. In general, the more viscous the dental bleaching composition, the more in situ foaming agent is required to yield a desired level of in situ foaming when placed over the teeth. Conversely, the less viscous the dental bleaching composition, the less in situ foaming agent will be required to yield a desired level of in situ foaming when placed over the teeth. Adding too much in situ foaming agent may result in premature and/or excessive foaming. Adding too little may inhibit or prevent adequate in situ foaming.

According to one embodiment, both the initial gel bleaching composition and the subsequent foam bleaching composition are sufficiently sticky as to adhere a dental bleaching tray or strip of material over a person's teeth. This in contrast to foamed compositions that exit a spray nozzle of a container already in the form of a foam. Such compositions generally include far greater quantities of entrained air bubbles and do not reliably adhere a dental tray or strip over a person's teeth.

Examples of other components that can be added to the in situ foamable dental bleaching compositions include stabilizing agents, neutralizing agents, buffering agents, desensitizing agents, remineralizing agents, antimicrobial agents, antiplaque agents, anti-tartar agents, other medicaments, flavorants, sweeteners, and the like. In one example embodiment, an in situ foamable dental bleaching composition includes a desensitizing agent such as potassium nitrate and/or a remineralizing agent such as a fluoride salt.

An example dental bleaching system includes the in situ foamable dental bleaching composition loaded within a pressurized container. According to one embodiment, the in situ foaming agent can create sufficient internal pressure within the container in order to express or dispense the bleaching composition as a gel upon release or actuation of a dispensing valve or nozzle. According to another embodiment, the pressurized container can be a "bag-on valve" that includes an interior bag with the foamable bleaching composition surrounded by a pressurized gas (e.g., air or nitrogen). In this way the propellant gas does not contact or mix with the foamable bleaching composition. In either case, the bleaching composition advantageously remains as a gel at room temperature and then foams in situ after being placed over a person's teeth and exposed to ambient heat within the person's mouth. The foamable dental bleaching composition may expand slightly upon being discharged from the pressurized container and then further expand and foam when applied to a person's teeth.

An example dental bleaching method includes (1) dispensing a dental bleaching gel from a container; (2) contacting tooth surfaces with the dental bleaching gel prior to foaming; (3) causing or allowing the bleaching gel to foam and expand in situ on the tooth surfaces as a result of ambient heat within a person's mouth; and (4) the foamed dental bleaching composition dynamically distributing and replenishing the bleaching agent on the tooth surfaces and into interproximal spaces between teeth.

An example kit according to the invention includes a container which holds therein an in situ foamable dental bleaching composition and one or more barrier layers for use in placing the in situ foamable dental bleaching composition over a person's tooth surfaces to be bleached. The one or more barrier layers are selected from customized dental treatment trays, non-custom dental treatment trays, and strips of a flexible material.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

The present invention relates to in situ foamable dental bleaching compositions that are formulated so as to be in the form of a gel when dispensed from a container at room temperature and then convert into a foam when contacted with a person's teeth. The inventive dental bleaching compositions include a low boiling in situ foaming agent that causes the dental bleaching composition to expand and form a foam when exposed to heat from a person's mouth (e.g., the foaming agent boils above room temperature and at or below body temperature).

Inventive dental bleaching systems include the in situ foamable dental bleaching composition within a pressurized container (e.g., a "bag-on valve" container). Inventive kits include the dental bleaching system and a plurality of barrier layers, such as dental trays and/or strips of material. Inventive methods include dispensing the in situ foamable dental bleaching composition in the form of a gel onto a surface of a barrier layer, placing the bleaching composition and barrier layer over a person's teeth, and allowing the in situ foamable dental bleaching composition to form a foam, which provides more available dental bleaching agent.

The term "barrier layer", as used herein, refers to one or more layers of a moisture-resistant material that protects the bleaching composition from ambient moisture and saliva found within a person's mouth when the dental bleaching device is placed over the person's teeth. The barrier layer may also serve to protect the bleaching composition from moisture or other contaminants during storage and prior to use. The barrier layer may be in any desired form including, but not limited to, a dental treatment tray or a flexible strip of material having no permanent shape.

The term "molecular weight", as used herein, refers to number average molecular weight expressed in Daltons unless otherwise specified.

II. In Situ Foamable Dental Bleaching Compositions

In situ foamable dental bleaching compositions according to the invention include a dental bleaching agent, a thickening agent in an amount so as to yield a composition that is in the form of a gel until expansion by an in situ foaming agent, an in situ foam agent, and a polyol-based carrier into which the dental bleaching agent, thickening agent, and in situ foaming agent are dispersed. The composition may optionally include other components as desired to yield a dental bleaching composition having desired properties.

The inventive compositions, apart from having the ability to foam when contacting a person's teeth during use, are stable, one-part compositions that can be stored for months or years within a pressurized container. The in situ foamable dental bleaching compositions advantageously have a pH in a range of about 5 to about 9, preferably from about 6 to about 7.

The in situ foamable dental bleaching compositions are formulated so as to have a viscosity and stickiness in order to reliably adhere a dental treatment tray or strip of material to a person's teeth. That is true for both the gel form of the composition before foaming and also the foamed form of the composition after foaming. The ability of the foamed composition to adhere a dental tray or strip of material to a person's teeth is in contrast to compositions that are designed to be a foam at the moment they are dispensed from an aerosol container.

While the in situ foamable dental bleaching compositions are designed to form a foam when contacted with a person's teeth, the amount of actual expansion is relatively small. The purpose of the in situ foaming action is to provide a more active composition in which the dental bleaching agent is more readily available for bleaching teeth. It is not intended to greatly increase the volume of the composition, as is typically the case where a foamed composition is dispensed from an aerosol container. Accordingly, the in situ foamable dental bleaching compositions are formulated so as to expand less than 25% by volume when contacted with a person's teeth, preferably less than about 20% by volume, more preferably less than about 15% by volume, and most preferably less than about 10% by volume.

According to one embodiment, the in situ foamable dental compositions are substantially free of abrasives (i.e., they contain less than 10% by weight of an abrasive, preferably less than about 5% by weight of an abrasive, more preferably less than about 3% by weight of an abrasive, and most preferably less than about 1% by weight of an abrasive).

A. Dental Bleaching Agents

Dental bleaching agents typically include a peroxide or peroxy compound. A common dental bleaching agent that is known to bleach teeth and that has been found to be safe for oral use is hydrogen peroxide. However, hydrogen peroxide does not itself exist in a stable form free in nature, but only as an aqueous solution or as a complex. Hydrogen peroxide complexes are typically more stable than aqueous hydrogen peroxide, though they may dissociate into hydrogen peroxide and the complexing salt when mixed with water. Even when added to water, complexed forms of hydrogen peroxide are often preferred because they are generally solid at room temperature and are therefore easier to handle in processes where it is desired to meter out a solid powder rather than a liquid.

Non-limiting examples of complexed hydrogen peroxide include carbamide (or urea) peroxide and metal perborates. Other bleaching agents that can be used to bleach teeth include, but are not limited to, metal percarbonates, peroxides (e.g., calcium peroxide and/or sodium peroxide), chlorites, and hypochlorites, peroxy acids, and peroxy acid salts.

Bleaching agents within the dental bleaching compositions according to the invention can have any desired concentration, e.g., between 1-90% by weight of the dental bleaching composition. The concentration of the dental bleaching agent can be adjusted depending on the intended treatment time for each bleaching session. In general, the shorter the treatment time, the more bleaching agent will be added to accelerate dental bleaching so as to effect bleaching in a shorter time period.

The dental bleaching agent is preferably included in an amount in a range of about 3% to about 30% by weight of the in situ foamable dental bleaching composition, more preferably in a range of about 5% to about 20% by weight of the in situ foamable dental bleaching composition, and most preferably in a range of about 8% to about 15% by weight of the in situ foamable dental bleaching composition.

B. Thickening Agents

Thickening agents within the scope of the invention include polyvinyl pyrrolidone (PVP), carboxypolymethylene, polyethylene oxide, polyacrylic acid polymers or copolymers, polyacrylates, polyacrylamides, copolymers of polyacrylic acid and polyacrylamide, PVP-vinyl acetate copolymers, carboxymethylcellulose, carboxypropylcellulose, polysaccharide gums, fumed silica, fumed alumina, and the like.

Examples of suitable thickeners that are substantially straight-chained include high molecular weight PVP and/or PEO, i.e., having a molecular weight greater than about 500,000. Utilizing PVP and/or PEO having a molecular weight greater than about 500,000 provides a composition can help adhere a barrier layer to the person's teeth. The PVP and/or PEO thickening agent will more preferably have a molecular weight greater than about 650,000, even more preferably greater than about 800,000, and most preferably greater than about 1,000,000.

One particularly preferred example of a PVP polymer that can be used in formulating bleaching compositions according to the invention is Kollidon 90 F, a PVP polymer having a molecular weight of about 1.3 million.

One particularly preferred example of a PEO polymer that can be used in formulating bleaching compositions according to the invention is POLYOX, a PEO polymer having a molecular weight of about 1.3 million made by Union Carbide.

The high molecular weight PVP and/or PEO is preferably included in an amount comprising at least about 5% by weight of the dental bleaching composition, more preferably at least about 10% by weight of the bleaching composition, and most preferably at least about 15% by weight of the bleaching composition. In one particularly preferred embodiment, the high molecular weight PVP and/or PEO is included in a range of about 15% to about 25% by weight of the dental bleaching composition.

Examples of other thickening agents include, but are not limited to, carboxypolymethylene (e.g., CARBOPOL, sold by Novean, Inc.), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, and the like. Cross-linked polymeric thickening agents such as carboxypolymethylene are preferably included in an amount comprising at least about 2% by weight of the dental bleaching composition, more preferably at least about 3.5% by weight of the bleaching composition, and most preferably at least about 5% by weight of the bleaching composition.

C. In Situ Foam Agents

The in situ foamable dental bleaching compositions include an in situ foaming agent that yields a stable gel when initially dispensed onto a barrier layer at room temperature and that causes the composition to foam when contacted with a person's teeth as a result of heating. According to one embodiment, the in situ foaming agent comprises a low boiling liquid such as isopentane. Isopentane is particularly beneficial as it boils at temperature of 28° C., which is above room temperature (i.e., 20-25° C.) and below body temperature (i.e., 37° C.).

The amount of isopentane is selected in order to provide a desired degree of foaming or expansion of the bleaching composition while preventing or inhibiting premature or excessive foaming. The isopentane is preferably included in a amount in a range of about 1% to about 8% by weight of the in situ foamable dental bleaching composition, more preferably in a range of about 1.25% to about 5% by weight, and most preferably in a range of about 1.5% to about 3% by weight of the in situ dental bleaching composition. According to one embodiment, the isopentane is included in an amount of about 2% by weight of the in situ dental bleaching composition.

In addition to isopentane, other in situ foaming agents may be included. Examples include other hydrocarbons having similar boiling points, such as pentane.

Ideally, the composition can exist as a gel at room temperature and only foams when heated to a temperature above room temperature (e.g., to a temperature of at least about 26° C., preferably at least about 28° C., more preferably at least about 30° C.). In some cases, however, the foamable dental bleaching compositions may expand slightly when initially dispensed from a pressurized container and then further expand and foam when contacted with a person's teeth.

It will be appreciated that the in situ foamable dental bleaching compositions preferably do not include significant quantities of propellant gasses or low boiling hydrocarbons that boil below room temperature, as such components would cause premature and/or excessive foaming of the dental bleaching composition (i.e., the compositions would exit the pressurized container as a highly foamed material rather than a gel). An important aspect of the invention is the ability of the in situ foamable dental bleaching compositions to be applied to a person's teeth as a gel and then expand and foam in situ on the person's teeth.

D. Polyol Based Carriers

The dental bleaching compositions also include at least one type of polyol based or containing carrier into which the dental bleaching agent, thickening agent, and in situ foaming agent are dispersed.

Examples of suitable constituents of the polyol based carrier include water, glycerin, liquid polyethylene glycol (e.g., MW of about 600), propylene glycol, 1,3-propane diol, xylotol, sorbitol, mannitol, and other polyols known in the art.

The polyol based carrier may be included in an amount in order to yield dental bleaching compositions having the desired rheological properties. In general, the polyol based carrier will comprise the balance of the composition after adding the dental bleaching agent, thickening agent, in situ foaming agent, and any optional components such as rheology modifying agents, remineralizing agents, desensitizing agents, an flavorts, bleaching agent stabilizers, neutralizing/buffering agents, and the like.

E. Other Components

The composition may include various other components to yield compositions having desired properties. Examples of other components include, but are not limited to, plasticizers and humectants, volatile solvents (e.g., alcohols such as ethanol), stabilizing agents (e.g., EDTA), neutralizing agents (e.g., sodium hydroxide), buffering agents (e.g., sodium phosphate and citric acid) desensitizing agents (e.g., potassium nitrate, other potassium salts, citric acid, citrates, and sodium fluoride), remineralizing agents (e.g., sodium fluoride, stannous fluoride, sodium monofluorophosphate, and other fluoride salts), antimicrobial agents (e.g., chlorhexidine, troclosan, and tetracycline), antiplaque agents, antitartar agents (e.g., pyrophosphates salts), other medicaments, flavorants, sweeteners, and the like.

A relatively small quantity of an inorganic, particulate rheology-modifying agent may optionally be included to improve the rheological properties of the compositions. According to one embodiment, the rheology-modifying agent is included to offset the stringiness imparted by high molecular weight PVP and/or PEO and also to reduce or eliminate runniness.

A currently preferred rheology-modifying agent is fumed silica, which comprises submicron sized particles. Fumed silica is characterized as having a particle diameter of about 0.04 micron to about 0.1 micron. An example of a suitable fumed silica is AEROSIL 200, made by Degussa of Germany. Other sub-micron particulate rheology-modifying agents that may be used within the scope of the invention include fumed alumina, barium oxide, strontium oxide, titanium dioxide, and zirconium dioxide. Fumed silica is preferred because it is the most stable when used in a dental bleaching composition. Fumed alumina is somewhat less stable than fumed silica.

The amount of fumed silica or other rheology-modifying agent is preferably included in an amount in a range of about 3% to about 15%, more preferably in a range of about 4% to about 12%, and most preferably in a range of about 5% to about 10%.

III. Dental Bleaching Systems

Figure 1:
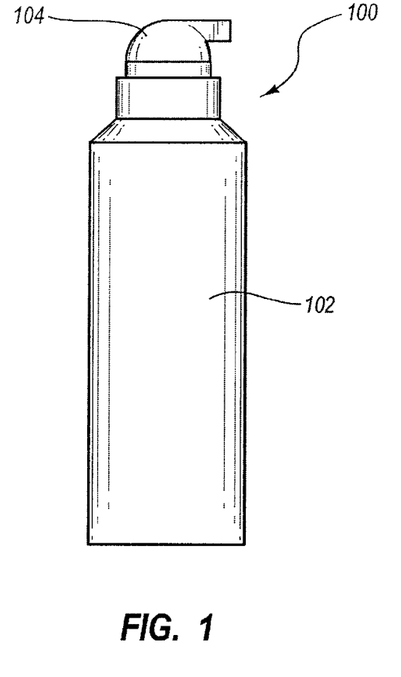
FIG. 1 illustrates an exemplary dental bleaching system composed of a pressurized container, an in situ foamable dental bleaching composition contained therein, and a dispensing nozzle.
Figure 2:
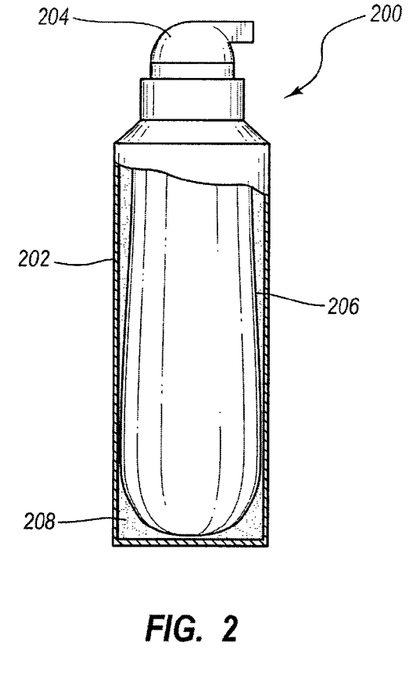
FIG. 2 illustrates an exemplary dental bleaching system composed of a pressurized bag-on valve container, an in situ foamable dental bleaching composition contained within an interior bag, a pressurized gas surrounding the interior bag, and a dispensing nozzle.
Figure 3A:
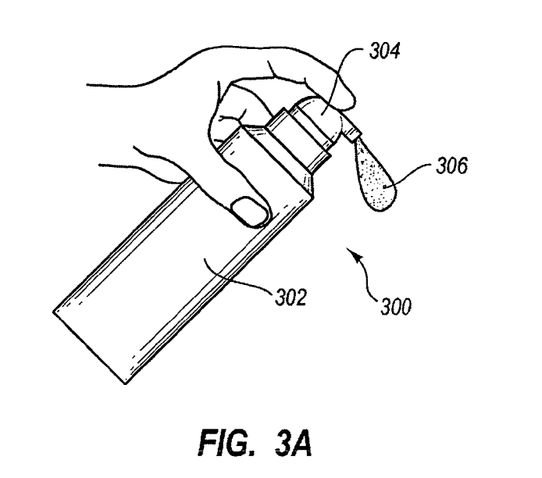
FIG. 3A illustrates an in situ foamable dental bleaching composition being dispensed from a pressurized container in the form of a gel.
Figure 3B:
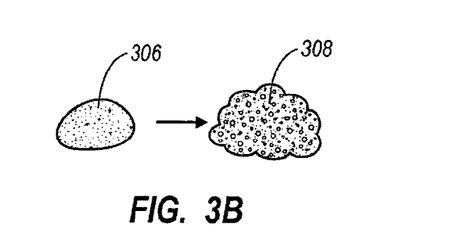
FIG. 3B illustrates an in situ foamable dental bleaching gel turning into a dental bleaching foam.

FIGS. 1-3 depict exemplary pressurized dental bleaching systems according to the invention. As illustrated in FIG. 1, a dental bleaching system 100 includes a pressurized container 102 containing the in situ foamable dental bleaching composition and a dispensing nozzle 104 through which the composition can be dispensed onto a barrier layer and/or a person's teeth. The dispensing nozzle 104 interacts with an internal valve to permit release of bleaching composition when the dispensing nozzle 104 is depressed or otherwise actuated.

FIG. 2 illustrates a dental bleaching system 200 that includes a "bag-on valve" container 202 and a dispensing nozzle 204 through which an in situ foamable dental bleaching composition can be dispensed onto a barrier layer and/or a person's teeth. The "bag-on valve" container 202 further includes an interior bag 206 that contains and isolates the in situ foamable dental bleaching composition from a pressurized gas located within the space 208 between the inner wall of container 200 and an outer wall of the interior bag 206. In this way, the pressurized gas (e.g., air or nitrogen) held within interior space 208 is isolated from and does not mix with the in situ foamable dental bleaching composition within the interior bag 206.

FIG. 3A depicts a dental bleaching system 300 having a pressurized container 302 and dispensing nozzle 304 in the process of being used to dispense a quantity of in situ foamable dental bleaching composition 306, which is initially in gel form with little or no foaming. Slight expansion of composition 306 may occur upon exiting the pressurized container 302 due to the drop in pressure to which the composition 306 is exposed. FIG. 3B schematically depicts a quantity of in situ foamable dental bleaching composition 306 being converted from a gel into an expanded foam composition 308. As shown, the composition 306 expands by approximately 25%, although the amount of actual expansion can be significantly less.

IV. Dental Bleaching Kits

Figure 4:
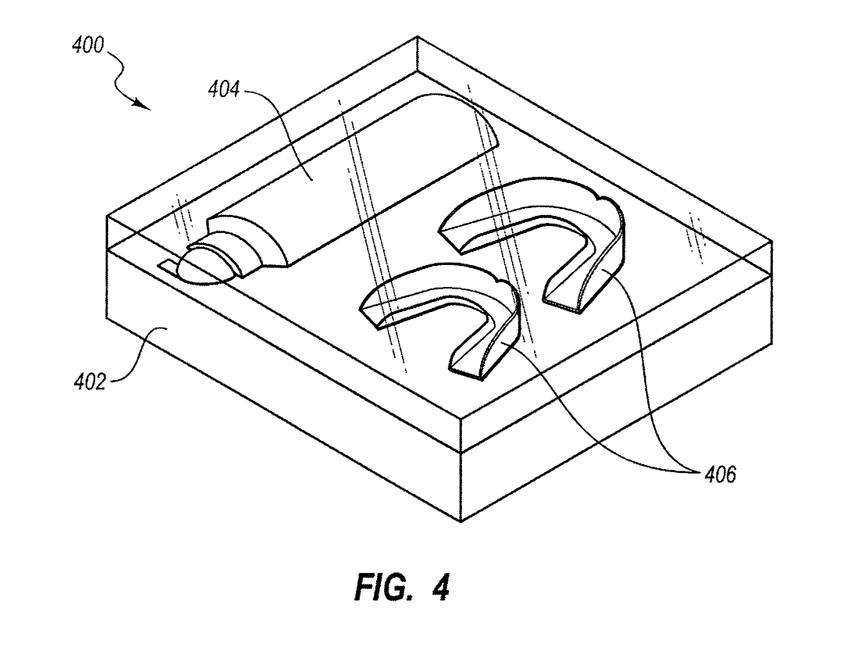
FIG. 4 illustrates an example kit including a dental bleaching system and a dental treatment tray.
Figure 5:
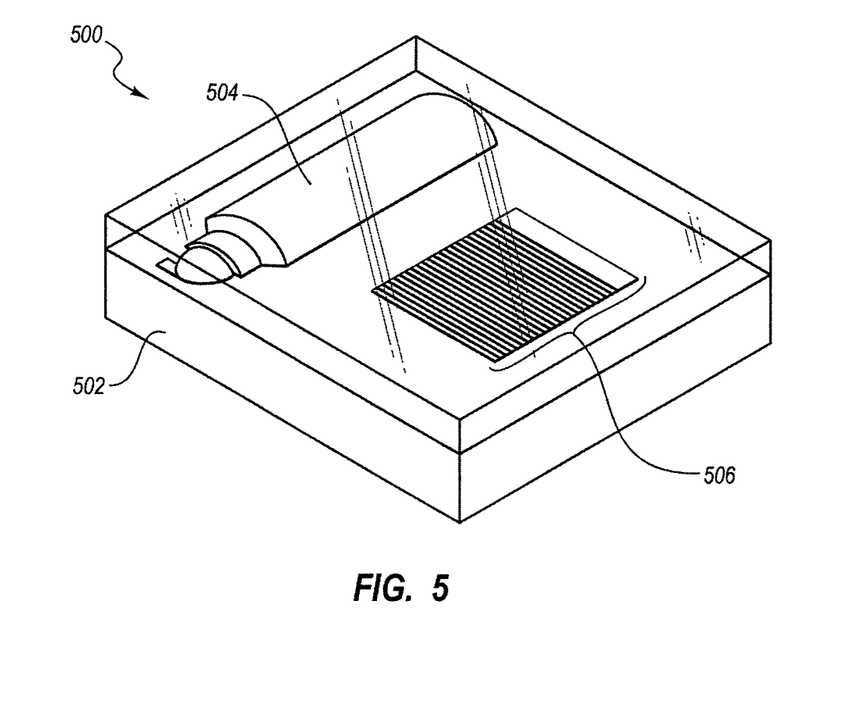
FIG. 5 illustrates an example kit including a dental bleaching system and a flexible strip of material.

Dental bleaching kits according to the invention are depicted in FIGS. 4 and 5. FIG. 4 shows a dental bleaching kit 400 that includes a kit container 402 having recesses formed therein for receiving therein a dental bleaching system 404 and a plurality of dental trays 406. Dental trays 406 can be customized trays that include recesses corresponding to the unique dentition of a person's teeth. Alternatively, dental trays can be non-customized trays that do not include recesses corresponding to the unique dentition of a person's teeth but rather are designed to be worn by a plurality of different people. As shown in FIG. 4, the kit may include two dental trays, one that fits over a person's upper teeth and one that fits over a person's lower teeth. Alternatively, the kit may include more than 2 dental trays in order to be usable by more than one person (e.g., a family).

FIG. 5 alternatively shows a dental bleaching kit 500 that includes a kit container 502 having recesses formed therein for receiving therein a dental bleaching system 504 and a plurality of treatment strips 506. As shown in FIG. 5, the kit may include a relatively large number of treatment strips 506 (e.g., 25 or more) in order for each strip to be disposable. The strips may be configured in different ways so that one is designed to comfortably fit over a person's upper teeth and another is designed to comfortably fit over a person's lower teeth.

Dental bleaching devices within the scope of the invention include a quantity of dental bleaching composition, as discussed above, disposed onto a barrier layer that is then placed over a person's teeth during dental bleaching.

According to one embodiment of the invention, the barrier layers can be formed from a moisture-resistant polymer material. In a currently preferred embodiment, the barrier layer comprises a thin, flexible layer of a polyolefin or similarly moisture-resistant material, such as wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes, polyesteramides, or mixtures thereof.

According to one embodiment, barrier layers can made from a proprietary material known as Parafilm®, which that is a blend of paraffin wax and polymer. Parafilm® is a product of the Pechiney Plastic Packaging Company, based in Chicago, Ill. It is stretchable, moldable, waterproof, odorless, thermoplastic, semitransparent and self-adhering. One type of Parafilm® material, known as Parafilm M®, is a semitransparent, flexible thermoplastic, and in its final form is a highly water proof and water resistant sheet material. It is practically colorless, odorless, tasteless and approximately 0.005" (e.g., 5 mils/127 μm) in thickness. The density of the film is reported to be 0.767 g/cc. The unique properties of Parafilm M® make it ideal and adaptable for use as a barrier layer. It is often used to cover test tubes in laboratory settings but has been discovered to be readily adaptable so as to seal itself around a person's teeth. Parafilm M® is described by the manufacturer as a blend of olefin-type materials.

Notwithstanding the foregoing, it is within the scope of the invention to provide barrier layers of any desired material, thickness or rigidity so long as the barrier layer provides at least some moisture protection relative to the bleaching composition. The barrier layer may comprise a conventional dental tray, examples of which include both customized and non-custom dental trays. The barrier layer may alternatively comprise a flexible strip of material have no permanent shape or shape memory.

Examples of suitable polyolefins for use in making the barrier layer include, but are not limited to, polyethylene (PE), high density polyethylene (HDPE), low density polyethylene (LDPE), ultra low density polyethylene (ULDPE), polypropylene (PP), and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. Plasticizers, flow additives, and fillers known in the art can be used as desired to modify the properties of any of the foregoing polymers used to form the barrier layer.

In general, dental trays that may be used within the scope of the invention will preferably have a wall thickness of less than about 1 mm, more preferably less than about 0.75 mm, and most preferably less than about 0.5 mm. Flexible strips for use in making bleaching strips will preferably have a cross-sectional thickness less than about 0.75 mm, more preferably less than about 0.5 mm, and most preferably less than about 0.2 mm.

In one embodiment, a tray-shaped barrier layer is preferred as it not only provides a barrier to protect the composition from the action of saliva or moisture found within the mouth, but it also is more easily placed over the teeth to be treated, readily covering the front, lingual, and interproximal spaces between adjacent teeth.

V. Exemplary Methods of Use

Figure 6:
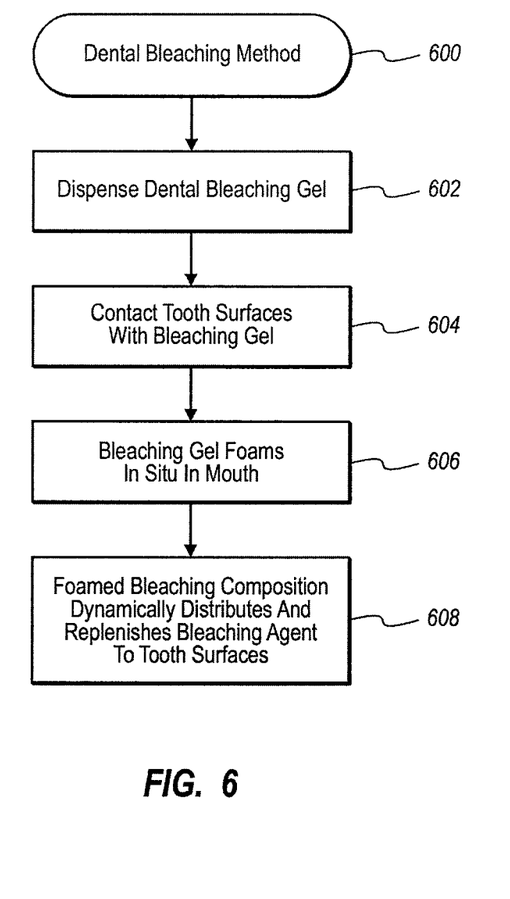
FIG. 6 is a flow chat illustrating an exemplary dental bleaching method.

FIG. 6 depicts a flow chart of an exemplary dental bleaching method 600. Method 600 includes the following steps: Step 602: dispensing an in situ foamable dental bleaching gel 602 (e.g., onto a barrier layer or directly over a person's teeth); Step 604: contacting tooth surfaces with the dental bleaching gel; step 606: or allowing the bleaching gel to foam in situ within the person's mouth; and step 608: the foamed dental bleaching composition dynamically distributes and replenishes the dental bleaching agent onto the person's tooth surfaces being bleached.

In a typical method, the in situ foamable dental bleaching composition is first applied to a barrier layer in the form of an unfoamed gel (although the gel may expand slightly when discharged from a pressurized container). Thereafter, the barrier layer with the gel is placed over a person's teeth. The gel has a stickiness and viscosity as to reliably adhere the barrier layer to the person's teeth. The heat contained within the person's mouth causes the gel composition to foam in situ, thereby yielding a foamed composition that increases the available and efficacy of the of dental bleaching agent compared to a non-foamed gel composition. The degree of foaming is sufficient to increase the dental bleaching effect while maintaining sufficient viscosity and stickiness so that the foamed composition continues to assist in adhering the tray to the person's teeth.

The dental bleaching device can be worn for as little as a few minutes and as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours.

Bleaching sessions may be repeated as many times as are needed to obtain a desired degree of whitening. A typical bleaching regimen will preferably include 1-20 bleaching sessions, more preferably 2-15 bleaching sessions, and most preferably 3-10 bleaching sessions.

VI. EXAMPLES

The following are several examples of in situ foamable bleaching compositions according to the invention. Such exemplary compositions are given by way of example, and not by limitation. Unless otherwise indicated, all percentages are by weight.

Example 1

An in situ foamable dental bleaching composition is formed by mixing together the following components:

| | |
|---|---|
| Carbamide Peroxide | 15.00% |
| Glycerin | 27.90% |
| Propylene Glycol | 48.00% |
| Carbomer | 3.50% |
| TRIS | 2.50% |
| Isopentane | 2.00% |
| Flavor | 1.00% |
| EDTA | 0.10% |

The resulting dental bleaching composition is a gel as room temperature and can be dispensed from a pressurized container as a gel at room temperature. The dental bleaching composition forms a foamed composition as a result of internal expansion by the isopentane upon being exposed to heat within a person's mouth.

Example 2

An in situ foamable dental bleaching composition is formed by mixing together the following components:

| | |
|---|---|
| Water | 20.00% |
| Carbamide Peroxide | 15.00% |
| Glycerin | 34.55% |
| Xylotol | 15.00% |
| Polyethylene Glycol | 5.00% |
| Carbomer | 5.00% |
| Sodium Hydroxide | 2.00% |
| Isopentane | 2.00% |
| Flavor | 0.50% |
| Sodium Saccharin | 0.10% |
| Sodium Fluoride | 0.25% |
| Potassium Nitrate | 0.50% |
| EDTA | 0.10% |

The resulting dental bleaching composition is a gel as room temperature and can dispensed from a pressurized container as a gel at room temperature. The dental bleaching composition forms a foamed composition as a result of internal expansion by the isopentane upon being exposed to heat within a person's mouth.

Example 3

An in situ foamable dental bleaching composition is formed by mixing together the following components:

| | |
|---|---|
| Water | 20.00% |
| Carbamide Peroxide | 35.00% |
| Glycerin | 26.00% |
| Xylotol | 5.00% |
| Carbomer | 5.00% |
| Sodium Hydroxide | 2.00% |
| Isopentane | 2.00% |
| Flavor | 0.50% |
| Sodium Saccharin | 0.10% |
| Sodium Fluoride | 1.10% |
| Potassium Nitrate | 3.00% |
| EDTA | 0.30% |

The resulting dental bleaching composition is a gel as room temperature and can be dispensed from a pressurized container as a gel at room temperature. The dental bleaching composition forms a foamed composition as a result of internal expansion by the isopentane upon being exposed to heat within a person's mouth.

Example 4

An in situ foamable dental bleaching composition is formed by mixing together the following components:

| | |
|---|---|
| Water | 30.00% |
| Hydrogen Peroxide | 10.00% |
| Glycerin | 10.70% |
| Xylotol | 5.00% |
| Carbomer | 7.50% |
| PVP | 18.00% |
| Silicon Dioxide | 9.00% |
| Sodium Hydroxide | 3.50% |
| Isopentane | 2.00% |
| Flavor | 2.00% |
| Sodium Saccharin | 2.00% |
| EDTA | 0.30% |

The resulting dental bleaching composition is a gel as room temperature and can be dispensed from a pressurized container as a gel at room temperature. The dental bleaching composition forms a foamed composition as a result of internal expansion by the isopentane upon being exposed to heat within a person's mouth.

Example 5

An in situ foamable dental bleaching composition is formed by mixing together the following components:

| | |
|---|---|
| Water | 20.00% |
| Carbamide Peroxide | 20.00% |
| Glycerin | 54.70% |
| Carbomer | 2.00% |
| Isopentane | 2.00% |
| Sodium Hydroxide | 1.20% |
| EDTA | 0.10% |

The resulting dental bleaching composition is a gel as room temperature and can be dispensed from a pressurized container as a gel at room temperature. The dental bleaching composition forms a foamed composition as a result of internal expansion by the isopentane upon being exposed to heat within a person's mouth.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental bleaching system for use in bleaching a person's teeth, comprising:
    a pressurized container; and
    a one-part in situ foamable dental bleaching composition comprised of:
        a dental bleaching agent;
        a thickening agent;
        an in situ foaming agent comprised of a low boiling liquid with a boiling point greater than 20° C.; and
        a polyol into which the dental bleaching agent, thickening agent, and in situ foaming agent are dispersed,
        the dental bleaching composition being formulated so as to be a gel when initially dispensed from the container at room temperature and thereafter expand so as to form a foam when contacted with a person's teeth and so that the gel expands by no more than approximately 25% by volume.

2. A dental bleaching system as defined in claim 1, wherein the dental bleaching agent comprises at least one of aqueous hydrogen peroxide, carbamide peroxide, calcium peroxide, a perborate, a percarbonate, or sodium chlorite.

3. A dental bleaching system as defined in claim 1, wherein the thickening agent comprises at least one member selected from the group consisting of polyvinyl pyrrolidone, carboxypolymethylene, polyethylene oxide, polyacrylic acid polymer or copolymer, polyacrylate, polyacrylamide, copolymer of polyacrylic acid and polyacrylamide, PVP-vinyl acetate copolymer, carboxymethylcellulose, carboxypropylcellulose, polysaccharide gum, fumed silica, and fumed alumina.

4. A dental bleaching system as defined in claim 1, wherein the thickening agent is included in an amount greater than about 2% by weight of the dental bleaching composition.

5. A dental bleaching system as defined in claim 1, wherein the thickening agent is included in an amount greater than about 5% by weight of the dental bleaching composition.

6. A dental bleaching system as defined in claim 1, wherein the thickening agent is included in an amount greater than about 10% by weight of the dental bleaching composition.

7. A dental bleaching system as defined in claim 1, wherein the polyol is selected from the group consisting of glycerin, propylene glycol, polyethylene glycol, 1,3-propane diol, polypropylene glycol, and xylotol.

8. A dental bleaching system as defined in claim 1, wherein the in situ foaming agent comprises at least one of isopentane or pentane.

9. A dental bleaching system as defined in claim 8, wherein the isopentane or pentane is included in an amount in a range of about 1% to about 8% by weight of the dental bleaching composition.

10. A dental bleaching system as defined in claim 8, wherein the isopentane or pentane is included in an amount in a range of about 1.25% to about 5% by weight of the dental bleaching composition.

11. A dental bleaching system as defined in claim 8, wherein the isopentane or pentane is included in an amount in a range of about 1.5% to about 3% by weight of the dental bleaching composition.

12. A dental bleaching system as defined in claim 8, wherein the composition is formulated so as to remain as a gel at a temperature of about 25° C. or below and form a foam in situ when heated to a temperature of about 26° C. or greater.

13. A dental bleaching system as defined in claim 8, wherein the composition is formulated so as to remain as a gel at a temperature of about 20° C. or below and form a foam in situ when heated to a temperature of about 28° C. or greater.

14. A dental bleaching system as defined in claim 8, wherein the composition is formulated so as to remain as a gel at a temperature of about 20° C. or below and form a foam in situ when heated to a temperature of about 30° C. or greater.

15. A dental bleaching system for use in bleaching a person's teeth comprising:
    a pressurized container; and
    a one-part in situ foamable dental bleaching composition comprised of:
        a peroxide dental bleaching agent;
        a thickening agent;
        an in situ foaming agent comprising at least one of isopentane or pentane; and
        a polyol carrier into which the dental bleaching agent, thickening agent, and in situ foaming agent are dispersed,
        the dental bleaching composition being formulated so as to be a gel when initially dispensed from the pressurized container at room temperature and thereafter expand so as to form a foam when contacted with a person's teeth, the gel expanding by no more than approximately 25% by volume.

16. A dental bleaching system as defined in claim 15, wherein the in situ dental bleaching composition is formulated so as to remain a gel at a temperature of about 25° C. or below and form a foam in situ when heated to a temperature of about 28° C. or greater.

17. A dental bleaching system as defined in claim 15, wherein the pressurized container is a bag-on valve comprising an interior bag that contains the in situ foamable dental bleaching composition and a pressurized gas surrounding an exterior of the interior bag.

18. A kit for use in bleaching a person's teeth comprising:
    the dental bleaching system of claim 15; and
    one or more barrier layers for use in applying and retaining the dental bleaching composition against a person's tooth surfaces.

19. A kit as defined in claim 18, wherein the barrier layer comprises a dental treatment tray.

20. A kit as defined in claim 18, wherein the barrier layer comprises a flexible strip of material.

21. A kit as defined in claim 18, wherein the barrier layer comprises a polymeric material.

22. A kit as defined in claim 21, wherein the polymeric material further includes a wax mixed therewith.

23. A method of bleaching a person's teeth, comprising:
providing the dental bleaching system of claim 1;
dispensing the in situ foamable dental bleaching composition, the bleaching composition being in gel form when initially dispensed from the container;
contacting the in situ foamable dental bleaching composition in gel form to a person's tooth surfaces; and
allowing the dental bleaching composition to expand and form a foamed dental bleaching composition on the person's tooth surfaces.

24. A method of bleaching a person's teeth as defined in claim 23, further comprising allowing the foamed dental bleaching composition to dynamically distribute and replenish the dental bleaching agent on the tooth surfaces.

25. A method of bleaching a person's teeth as defined in claim 23, the in situ foamable dental bleaching composition expanding slightly when dispensed from the pressurized container and then further expanding and foaming after contacting the person's tooth surfaces.

26. A dental bleaching system for use in bleaching a person's teeth, comprising:
a bag-on valve container comprising an interior bag that contains an in situ foamable dental bleaching composition and a pressurized gas surrounding an exterior of the interior bag; and
an in situ foamable dental bleaching composition disposed within the interior bag and comprised of:
a dental bleaching agent;
a thickening agent;
an in situ foaming agent comprised of a low boiling liquid with a boiling point greater than 20° C.; and
a polyol into which the dental bleaching agent, thickening agent, and in situ foaming agent are dispersed,
the dental bleaching composition being formulated so as to be a gel when initially dispensed from the container at room temperature and thereafter expand so as to form a foam when contacted with a person's teeth and so that the gel expands by no more than approximately 25% by volume.

* * * * *

UNITED STATES PATENT AND TRADEMARK OFFICE
CERTIFICATE OF CORRECTION

PATENT NO. : 8,414,868 B2
APPLICATION NO. : 12/700197
DATED : April 9, 2013
INVENTOR(S) : Andersen Page 1 of 2

It is certified that error appears in the above-identified patent and that said Letters Patent is hereby corrected as shown below:

In the Specification

Column 1
Line 36, change "Gel bleaching composition" to --Gel bleaching compositions--
Line 37, change "better able adhere" to --better able to adhere--
Line 56, change "person's tooth surfaces" to --person's teeth surfaces--
Line 58, change "person's tooth surfaces" to --person's teeth surfaces--

Column 2
Line 19, change "providing" to --provide--

Column 4
Line 40, change "flow chat" to --flow chart--
Line 50, change "then convert" to --then converted--

Column 7
Line 50, change "gasses" to --gases--

Column 8
Line 37, change "sub-micron" to --submicron--
Line 67, change "container 200" to --container 202--

Column 9
Line 32, change "more than 2" to --more than two--
Line 65, change "water proof" to --waterproof--

Column 10
Line 14, change "material have" to --material that has--
Line 46, change "bleaching gel 602" to --bleaching gel--

Signed and Sealed this
Twentieth Day of May, 2014

Michelle K. Lee
*Deputy Director of the United States Patent and Trademark Office*

CERTIFICATE OF CORRECTION (continued)
U.S. Pat. No. 8,414,868 B2

Line 47, change "teeth); Step" to --teeth); step--
Line 48, change "or allowing" to --allowing--

Column 11
Line 2, change "few minutes and" to --few minutes or--